US012151048B2

(12) United States Patent
Hughes et al.

(10) Patent No.: US 12,151,048 B2
(45) Date of Patent: *Nov. 26, 2024

(54) BIOERODIBLE CROSS-LINKED HYDROGEL IMPLANTS AND RELATED METHODS OF USE

(71) Applicant: Dose Medical Corporation, San Clemente, CA (US)

(72) Inventors: Patrick Michael Hughes, Aliso Viejo, CA (US); Ina Mustafaj, Irvine, CA (US)

(73) Assignee: DOSE MEDICAL CORPORATION, San Clemente, CA (US)

( * ) Notice: Subject to any disclaimer, the term of this patent is extended or adjusted under 35 U.S.C. 154(b) by 194 days.

This patent is subject to a terminal disclaimer.

(21) Appl. No.: 17/808,412

(22) Filed: Jun. 23, 2022

(65) Prior Publication Data

US 2022/0323650 A1   Oct. 13, 2022

Related U.S. Application Data

(63) Continuation of application No. 16/985,668, filed on Aug. 5, 2020, now Pat. No. 11,383,006.
(Continued)

(51) Int. Cl.
*A61L 27/44* (2006.01)
*A61K 9/00* (2006.01)
(Continued)

(52) U.S. Cl.
CPC .......... *A61L 27/446* (2013.01); *A61K 9/0048* (2013.01); *A61K 9/0051* (2013.01);
(Continued)

(58) Field of Classification Search
None
See application file for complete search history.

(56) References Cited

U.S. PATENT DOCUMENTS 6,632,457 B1   10/2003   Sawhney
7,413,752 B2   8/2008    Sawhney
(Continued)

FOREIGN PATENT DOCUMENTS

WO   2017015616   1/2017
WO   2021026214   2/2021

OTHER PUBLICATIONS

Jian-Guo Sun et al. "Mesoporous silica nanoparticles as a delivery system for improving antiangiogenic therapy." International Journal of Nanomedicine, vol. 14, 2019, pp. 1489-1501. (Year: 2019).*
(Continued)

*Primary Examiner* — Isaac Shomer
(74) *Attorney, Agent, or Firm* — Stoel Rives LLP

(57) ABSTRACT

The present disclosure is directed to a composite implant for the sustained release of a therapeutic agent from a hydrogel matrix. The hydrogel matrix may be a cross-linked bioerodible polyethylene glycol (PEG) hydrogel with a therapeutic complex dispersed within the cross-linked bioerodible PEG hydrogel. The therapeutic complex may include a therapeutic agent in association with mesoporous silica particles. The composite implant is configured to be delivered to or implanted into an eye of a subject or patient. The composite implant may be used treat ocular disease in a subject or patient. Ocular diseases may be selected from at least one of neovascular age related macular degeneration (AMD), diabetic macular edema, or macular edema following retinal vein occlusion.

16 Claims, 10 Drawing Sheets

Related U.S. Application Data

(60) Provisional application No. 62/883,493, filed on Aug. 6, 2019.

(51) Int. Cl.
*A61L 27/52* (2006.01)
*A61L 27/54* (2006.01)
*C08L 71/02* (2006.01)

(52) U.S. Cl.
CPC .............. *A61L 27/52* (2013.01); *A61L 27/54* (2013.01); *A61L 2400/06* (2013.01); *C08L 71/02* (2013.01)

(56) References Cited

U.S. PATENT DOCUMENTS

| | | | |
|---|---|---|---|
| 8,007,459 B2 | 8/2011 | Haffner et al. | |
| 9,205,150 B2 | 12/2015 | Jarrett et al. | |
| 9,254,267 B2 | 2/2016 | Sawhney | |
| 11,383,006 B2* | 7/2022 | Hughes | A61K 9/146 |
| 2003/0223957 A1* | 12/2003 | Schwartz | A61L 24/046 424/78.38 |
| 2010/0209478 A1 | 8/2010 | Sawhney et al. | |
| 2011/0054441 A1 | 3/2011 | Erickson et al. | |
| 2014/0012177 A1 | 1/2014 | Tu et al. | |
| 2016/0136088 A1 | 5/2016 | Jokinen et al. | |
| 2016/0331738 A1 | 11/2016 | Jarrett et al. | |
| 2017/0087248 A1* | 3/2017 | Kang-Mieler | A61K 38/1866 |
| 2018/0361030 A1 | 12/2018 | Ferrari et al. | |
| 2021/0038769 A1 | 2/2021 | Hughes et al. | |

OTHER PUBLICATIONS

Sun JG et al. https://www.dovepress.com/mesoporous-silica-nanoparticles-as-a-delivery-system-for-improving-ant-peer-reviewed-fulltext-article-IJN accessed Mar. 26, 2024, originally published Feb. 25, 2019, pp. 1-6. (Year: 2019).*
Timothy W. Olsen, et al. "Pharmacokinetics of Pars Plana Intravitreal Injections versus Microcannula Suprachoroidal Injections of Bevacizumab in a Porcine Model." Investigative Ophthalmology & Visual Science, Jun. 2011, vol. 52, No. 7, pp. 4749-4756. (Year: 2011).*
Kaihui Nan, Feiyan Ma, Huiyuan Hou, William R. Freeman, Michael J. Sailor, Lingyun Cheng. "Porous silicon oxide-PLGA composite microspheres for sustained ocular delivery of daunorubicin." Acta Biomaterialia, vol. 10, 2014, pp. 3505-3512. (Year: 2014).*
Changhai Lu, Payam Zahedi, Adam Forman, and Christine Allen. "Multi-arm PEG/Silica Hydrogel for Sustained Ocular Drug Delivery." Journal of Pharmaceutical Sciences, vol. 103, 2014, pp. 216-224. (Year: 2014).*
Food and Drug Administration. "Biosimilar and Interchangeable Products." https://www.fda.gov/drugs/biosimilars/biosimilar-and-interchangeable-products accessed Feb. 24, 2022, pp. 1-5 (Year: 2022).*
Biosimilar and Interchangeable Products, Food and Drug Administration, https://www.fda.gov/drugs/biosimilars/biosimilar-and-interchangeable-products accessed Feb. 24, 2022, pp. 1-5 (Year 2022).
Calvo, et al., The US Approach to Biosimilars—The Long Awaited FDA Approval Pathway, Current Opinion—Biodrugs 2012, 26 (6)357-361.
Chang, et al., Hydrogels for sustained delivery of biologics to the back of the eye, Drug Delivery Today, vol. 24, No. 8, Aug. 2019, pp. 1470-1482 (Year: 2019).
Henise, et al., Biodegradable Tetra-PEG Hydrogels as Carriers for a Releasable Drug Delivery System, Bioconjugate Chemistry, 2015, vol. 26, 270-278.
Hu, et al., Polysaccharides/mesoporous silica nanoparticles hybrid composite hydrogel beads for sustained drug delivery, Journal of Materials Science, vol. 52, 2017, pp. 3095-3109. (Year: 2017).
Katiyar, et al., Synthesis of ordered large pore SBA-15 spherical particles for adsorption of biomolecules, J. Chromatogr. A 1122 (2006) 13-20.
Kong, et al., Polyethylene glycol as a promising synthetic material for repair of spinal cord injury, Jun. 12, 2017 (Jun. 12, 2017), Neural Regen Res. Jun. 2017; 12(6); 1003-1008, doi:10.4103/1673-5374. 208597.
Liao, et al., Gelatin-functionalized mesoporous silica nanoparticles with sustained release properties for intracameral pharmacotherapy of glaucoma, Journal of Materials Chemistry B, vol. 5, 2017, pp. 7008-7013 (Year: 2017).
Lu, et al., Multi-arm PEG/Silica Hydrogel for Sustained Ocular Drug Delivery, Journal of Pharmaceutical Sciences, vol. 103, 2014, pp. 216-226 (Year: 2014).
Nan, et al., Porous silicon oxide-PLGA composite microspheres for sustained ocular delivery of daunorubicin, Acta Biomaterialia, vol. 10 (2014), pp. 3505-3512, (Year: 2014).
Olsen, et al., Pharmacokinetics of Pars Plana Intravitreal Injections versus Microcannula Suprachoroidal Injections of Bevacizumab in a Porcine Model, Investigative Ophthalmology & Visual Science, Jun. 2011, vol. 52, No. 7, 4749-4756.
Osswald, et al., Controlled and extended in vitro release of bioactive anti-vascular endothelial growth factors from a microsphere-hydrogel drug delivery system, Current Eye Research, vol. 41, No. 9, 2016, pp. 1216-1222 (Year: 2016).
Sun, et al., Mesoporous silica nanoparticles as a delivery system for improving antiangiogenic therapy, Dovepress, International Journal of Nanomedicine, 2019, vol. 4, 1489-1501.
Zustiak, et al., Characterization of Protein Release from Hydrolytically Degradable Poly(Ethylene Glycol) Hydrogels, Biotechnology and Bioengineering, vol. 108, No. 1, Jan. 1, 2011, pp. 197-206. (Year: 2011).
European Patent Office: Supplementary European Search Report for European Patent Application No. 20850063.7, issued Jul. 3, 2023, 10 pages.
Lei Lei, et al.,"Injectable Colloidal Hydrogel with Mesoproous Silica Nanoparticles for Sustained co-release of MiroRNA -222 and Aspirin to Achieve Innerted Bone Regeneration in Rat Mandibular Defects", Journal of Materials Chemistry, B, vol. 7, No. 16, Jan. 1, 2019, 14 pages.
Park,J. et al., "The Effect of Silica Nanoparticles on Human Corneal Epithelial Cells", Scientific Reports, vol. 6, No. 1, retrieved from Internet: URL:https://www.nature.com/articles/srep37762.pdf, Nov. 23, 2016, 1 pages.
Sooyeaon,K. et al., "Silica-Based Mesoporous Nanoparticles for Controlled Drug Delivery", Journal of Tissue Engineering, retrieved from Internet: URL:https://journals.sagepub.com/doi/pdf/10.1177/ 2041731413503357, Jan. 1, 2013, 18 pages.
Yang Shengbing, et al., "Mechanically Robust PEGDA-MSNs-OH Nanocomposite Hydrogel with Hierarchical Meso-Macroporous Structure for Tissue Enginerring", Soft Matter, vol. 8, No. 34, Jan. 1, 2012, 9 pages.
Changhai, et al., Multi-arm PEG/Silica Hydrogel for Sustained Ocular Drug Delivery, Journal of Pharmaceutical Sciences, 103:216-226, 2014.
Drapala, et al., Role of Thermo-responsivness and Poly()ethylene glycol) Diacryalate Cross-link Density on Protein Release from Poly(N-isopropylacrylamide) Hydrogels, Journal of Biomaterials Science, vol. 22 (2011), pp. 59-75 (Year 2011).
Japan Patent Office, Office Action Received in Japanese Patent Application No. 2022-507540, mailed Aug. 6, 2024, 10 pages.
Yang, S. , et al., Soft Matter, Mechanically robust PEGDA-MSNs-OH nanocomposite hydrogel with hierarchical meso-macroporous structure for tissue engineering, vol. 8, No. 34, pp. 8981-8989, Jan. 17, 2012.

* cited by examiner

BIOERODIBLE CROSS-LINKED HYDROGEL IMPLANTS AND RELATED METHODS OF USE

RELATED APPLICATIONS

This application claims priority to U.S. patent application Ser. No. 16/985,668 and titled BIOERODIBLE CROSS-LINKED HYDROGEL IMPLANTS AND RELATED METHODS OF USE, filed on Aug. 5, 2020, which claims priority to U.S. Provisional Patent Application No. 62/883,493, filed Aug. 6, 2019, and titled BIOERODIBLE CROSS-LINKED HYDROGEL IMPLANTS AND RELATED METHODS OF USE, both of which are incorporated herein by reference in its entirety.

TECHNICAL FIELD

The present disclosure relates to composite implants for treating ocular diseases, such as neovascular age-related macular degeneration (AMD), diabetic macular edema, and macular edema following retinal vein occlusion. In particular, the composite implants include a composition that provides sustained release of a therapeutic complex from a composite mesoporous silica and bioerodible hydrogel matrix. The present disclosure further relates to methods for making and manufacturing bioerodible cross-linked hydrogel implants, as well as related methods of using the bioerodible cross-linked hydrogel implants.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Figure 1:
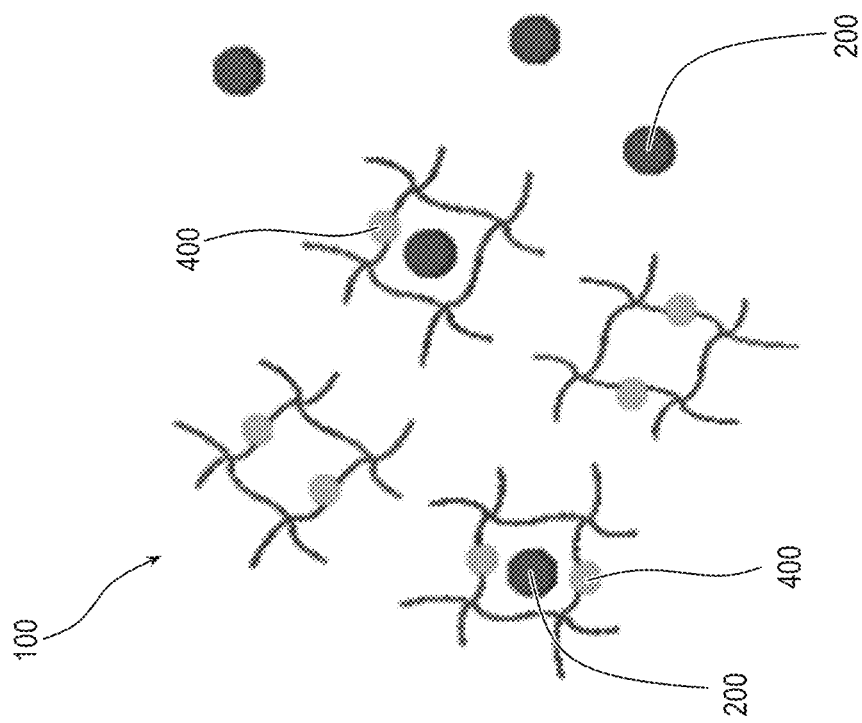
FIG. 1 illustrates a schematic of a cross-linked composite implant with a cross-linked polymer with a degradable linkage and a therapeutic complex, according to one embodiment.
Figure 1:
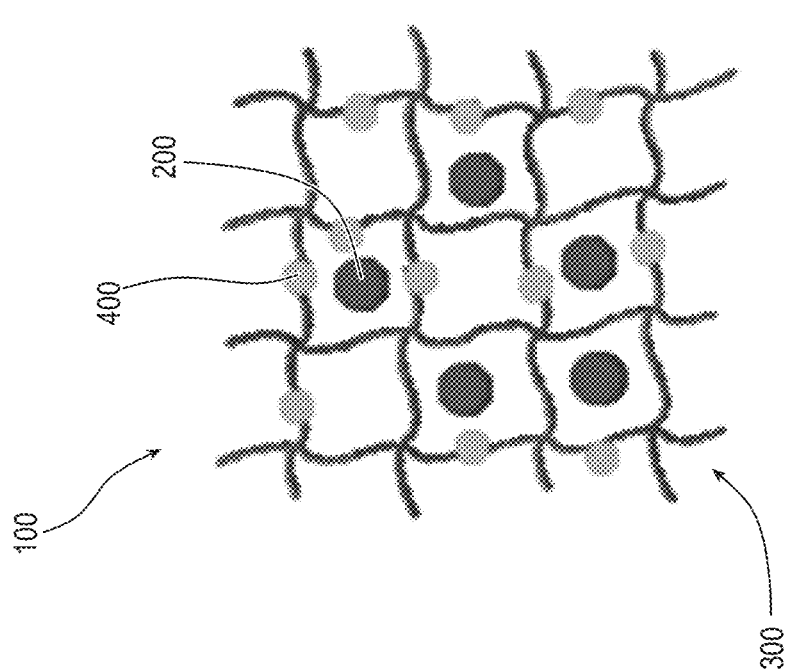

Proteins are attractive therapeutic targets due to their specificity and potency. Biologics such as proteins are becoming increasingly important in medicine. In ophthalmology, several biologics have had tremendous therapeutic impact. Bevacizumab, ranibizumab, and aflibercept are examples of proteins that have been shown to provide great clinical benefit in subjects having diseases such as neovascular AMD and diabetic macular edema.

Proteins are hydrophilic, water soluble macromolecules that have poor membrane permeation. As such, the bioavailability of proteins from oral administration or topical administration is poor. To circumvent the absorption barriers for proteins, they are usually administered by parenteral administration or direct injection into the desired biologic compartment, such as intraocular administration. There are several constraints to productive absorption of therapeutic proteins into the eye. Topically, macromolecules such as proteins will have limited permeability to the corneal epithelium and a rapid pre-corneal clearance from topical dosing. Typically, only 1% to 5% of a topically administered small molecule eye drop is bioavailable to the aqueous humor. Topical bioavailability of proteins is considerably less. Further movement to the posterior segment of the eye is limited by the iridolenticular diaphragm and the diffusional barrier presented by the vitreous. Hence, little to no topically applied drug can reach the posterior segment of the eye by the macula. The blood-retinal barriers and blood-aqueous barriers further prevent intraocular uptake of proteins from systemic administration. The proteins to be administered require intravitreal injection to achieve therapeutic concentrations in the posterior segment of the eye.

Proteins also suffer from rapid clearance from the systemic circulation. While the clearance of proteins from the vitreous is slower, with half-lives on the order of days, they are still cleared rapidly relative to the duration of therapy. This requires proteins to be injected into the eye at high concentrations to prolong therapeutic effect and by frequent monthly or bi-monthly injections. The result is transient high initial intraocular concentrations of the protein, which can lead to unintended side effects and frequent intravitreal injections that increase the risk for endophthalmitis, cataract, retinal detachment, and other detrimental sequelae.

Therefore, sustained delivery of proteins directly to the intraocular space would greatly improve the therapeutic benefit to patients. Despite the high medical value of sustained protein delivery systems to the eye, no system has been successfully developed. Sustained delivery of proteins offers several unique challenges. Proteins are sensitive to aggregation and potential immunogenicity issues, denaturation, and loss of activity and degradation. This can be brought about by the sheer and thermal stresses encountered during manufacturing, aggregation and degradation in aqueous environments, loss of tertiary and quaternary structure and activity, and losses to interfaces. Most proteins are sensitive to extremes of pH. Poly-lactide-co-glycolide, polycaprolactone, and other polyester bioerodible polymers are commonly used to formulate sustained release delivery systems. Unfortunately, proteins can degrade, aggregate, or lose activity at the hydrophobic interfaces during manufacture of the delivery system, upon hydration of the delivery systems and protein release, or in the acidic microenvironment created as these polymers degrade in vivo.

Hydrogels provide an attractive alternative to polyesters because they create a protein friendly environment and acidic products of degradation can diffuse away prior to affecting the protein. However, hydrogels have a high water content that can cause protein degradation and aggregation. Hydrogels are also relatively porous, rendering it difficult to control the protein release. Our work has shown that cross-linked PEG hydrogels, by themselves, do not provide sustained protein release beyond a few months and that protein aggregates and degrades within 30 days in an aqueous environment.

A composite system of the cross-linked bioerodible PEG hydrogel and aflibercept loaded mesoporous silica particles to enable sustained release for several months and maintain the stability of the released protein is described herein. However, the present disclosure is not so limited, and other mesoporous materials may be used to load the protein.

Entrapping the mesoporous silica particles loaded with a therapeutic protein in a cross-linked hydrogel matrix allows for active protein to be released over a period of weeks to months. Forming the hydrogel involves reacting PEG-amine with PEG-SG, PEG-SAP, and/or a PEG-SAZ monomers to form crosslinks. Each chemistry has its own crosslink density and subsequent rate of degradation, and so selecting the composition of the reactive PEGs allows for tuning of the biodegradation of the hydrogel, and release of its contents, from weeks to months. Also affecting the primary release rate are the molecular weights of the PEG monomers and the crosslinking density. 4-arm and 8-arm PEG monomers with molecular weights of 5 kDa or 10 kDa may be used.

Mesoporous silica particles can stabilize the protein and cause sustained release within the PEG hydrogel. Mesoporous silica particles entrap the protein molecules within the mesopores or adsorb the protein to the outer surface in order to reduce mobility and minimize aggregation. They have high drug-loading capacity due to their large surface area and well-defined surface properties, allowing for functionalization of the silanol-containing surface to control drug release. Mesoporous silica particles can be fabricated via electrochemical etching of silicon wafers or synthesized using sol-gel methods such as surfactant templating. The particle size, shape, pore size and porosity can be tuned to the morphology and size of the loaded drug.

Mesoporous silica particles can be synthesized in the presence of surfactants, which act as templates to direct the morphology of final amorphous material. The surfactants are dissolved into polar solvents to a concentration above critical micellar concentration, causing the molecules to self-assemble into micelles. Once the micelles are formed, silica precursors, such as tetraethyl orthosilicate (TEOS) are added to the suspension, after which sol gel reaction takes place. The surfactants are then removed by calcination or extraction. The structure size and morphology of the mesoporous silica particles depend on choice of catalyst, pH, water to silica precursor ratio, type of solvent, solvent to water ratio, type of silicon precursor, and temperature of synthesis and aging. Mobile Composition of Matter 41 (MCM-41) and Santa Barbara Amorphous 15 (SBA-15) are common types of mesoporous silica particles, consisting of an ordered hexagonal arrangement of cylindrical pores. MCM-41 use cetyl trimethyl ammonium bromide (CTAB) as the surfactant and SBA-15 typically utilizes pluronics such as P123.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

FIG. 1 provides a schematic illustration of a portion of a composite implant 100 for the sustained release of a therapeutic agent 200 from a hydrogel matrix 300. The hydrogel matrix 300 may include degradable linkages 400 that enable the release of the therapeutic agent 200 from the hydrogel matrix 300 over time. In some embodiments, the hydrogel matrix 300 may be a cross-linked bioerodible polyethylene glycol (PEG) hydrogel with a therapeutic complex dispersed within the cross-linked bioerodible PEG hydrogel. The therapeutic complex may include a therapeutic agent 200 in association with mesoporous silica and/or any other excipients, peptides, or nucleic acids. The composite implant 100 may be configured to be delivered to or implanted into an eye of a subject or a patient. The composite implant 100 may comprise a rod shape, or other shape as desired.

The composite implant may be used to treat ocular diseases in a subject or a patient. Ocular diseases may be selected from at least one of neovascular AMD, diabetic macular edema, and macular edema following retinal vein occlusion. Other ocular diseases that may be treated by the composite implant include, but are not limited to, proliferative vitreal retinopathy, dry AMD, glaucoma (neuroprotection), uveitis, vitritis, endophthalmitis, infection, inflammation, cataract, retinitis pigmentosa, chorioretinitis, choroiditis, and autoimmune disorders.

The therapeutic complex may include a therapeutic agent associated with a mesoporous silica. In particular embodiments, the association between the therapeutic agent and the mesoporous silica particles in the therapeutic complex can be achieved by various means, such as hot melt extrusion, blending, compression, granulation, roller compaction, spray drying, co-lyophilization, spray freeze drying, microencapsulation, melt encapsulation, coacervation, solvent casting, microfluidics, injection molding, and/or other method for fabricating microparticles and the like. In certain embodiments, the therapeutic complex may be composed of the therapeutic agent dispersed within, coated by, and/or adsorbed to the mesoporous silica particles. The therapeutic agent may be at least one of a protein, a peptide, a nucleic acid, an RNA, an siRNA, aptamers such as pegaptanib, or a small molecule. The therapeutic agent may include at least one of a prostaglandin, a neuroprotectant, a retinoid, squalamine, a steroid, an alpha adrenergic agent, a gene, an antibiotic, a non-steroidal anti-inflammatory agent, a calcineurin inhibitor such as cyclosporine, an adeno-associated virus vector, a tyrosine kinase inhibitor, or a rho kinase inhibitor.

The therapeutic protein/peptide may include, but is not limited to, bevacizumab, ranibizumab, aflibercept, brolucizumab, faricimab, conbercept (recombinant anti-VEGF fusion protein), ankyrin repeat proteins such as abicipar pegol, adalimumab and other anti-TNF-alpha agents, biosimilars, their respective salts, esters, solvates, isomers, or complexes, and conjugates such as pegylation. In some embodiments, the therapeutic protein/peptide may include, but is not limited to ranibizumab, aflibercept, brolucizumab, faricimab, and conbercept.

The hydrogel serves to sequester the therapeutic complexes and to modulate the release of the protein from the composition. The therapeutic complexes comprise mesoporous microparticles loaded with protein. The hydrogel further shields the protein-loaded mesoporous silica particles from the body's immune response and enzymes. The mesoporous silica particles stabilize the protein to manufacturing processes and the aqueous environment in vivo during release as well as to provide a sustained or controlled release of the therapeutic protein. Agents such as excipients, release modifiers, surfactants amongst others can be incorporated into the composition.

Mesoporous silica particles can be produced by numerous different processes including surfactant templating and acid etching of silicon wafers. Another method of producing mesoporous silica particles is electrochemical anodization of silicon wafers in a hydrofluoric acid electrolyte solution. Mesoporous silica particles with pores ranging from 1 nm to several micrometers can be produced by this method. Process parameters that affect mesoporous silica particles include the current density, type and amount of dopant, and electrolyte concentration.

Mesoporous silica can also be produced by the surfactant templating technique. Surfactant micelles can be produced in a polar media using cationic alkylammonium surfactants such as cetrinium bromide (cetyl trimethyl ammonium bromide, CTAB) or block co-polymers such as pluronic surfactants, poly(ethylene oxide)-poly(propylene oxide)-poly(ethylene oxide) (PEO-PPO-PEO) block copolymers. Once micelles are formed the mesoporous silica particles are produced by condensation of silica precursors around the surfactant templates. Esters of orthosilicic acid are common silica sources such as tetraethoxysilane (TEOS). The condensation reaction can be catalyzed by acidic and basic conditions as well as the addition of ammonium fluoride. Once the reaction is complete the surfactant as well as any co-surfactants or swelling agents can be removed by extraction or calcination at high heat. Two types of surfactant template produced mesoporous silica particles are Mobile Composition of Matter-41 (MCM-41) and Santa Barbara Amorphous-15 (SBA-15).

Process parameters that can be adjusted to modify the pore size, pore structure and order and particle morphology of the mesoporous silica particles include the condensation reaction temperature, surfactant type, co-surfactant, swelling agents, aging temperature, hydrothermal swelling and calcination time and temperatures.

Swelling agents can partition into the hydrophobic core of the surfactant micelles making larger pores during the silica condensation. Trimethylbenzene (TMB) is a common swelling agent used in the production of large pore mesoporous silica particles. Alkanes, cyclic alkanes, aromatics, aromatic alcohols and alkane alcohols are also often used as swelling agents. Co-surfactants can be utilized to modify the morphology of the mesoporous silica particle.

The pore size, pore structure and order, and the mesoporous silica particle size and morphology can affect their performance. Barrett, Joyner, and Halenda (BJH) gas sorption isotherms can be used to calculate the average pore size of the mesoporous silica particles. Small angle x-ray diffraction (SAX) can be used to determine the pore size, size distribution, pore structure and pore spacing.

The mesoporous silica particles can be loaded with active compounds by many means. The incipient wetness method involves adding a known volume of drug loaded liquid to the mesoporous silica particles and allowing it to sorb. Actives can also be loaded by incubating the mesoporous silica particles in a solution of the active then filtering and vacuum drying or freeze drying the loaded particles. Adsorption from organic solvents is also a common method of loading the particles. Methods such as melt loading, spray drying and other processes known in the art can be used to load the mesoporous silica particles.

Figure 2:
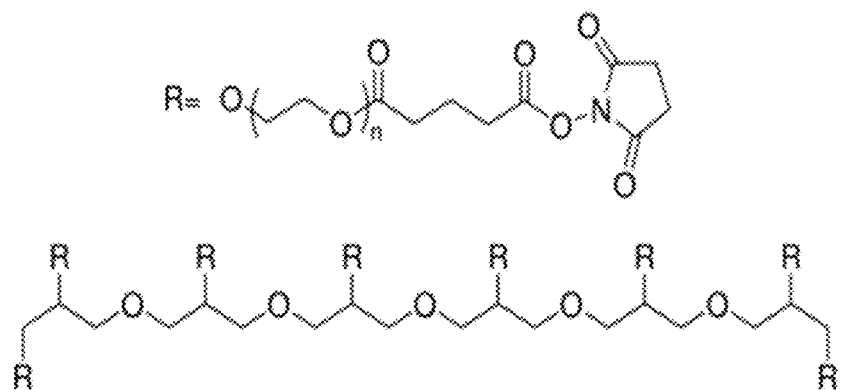
FIG. 2 illustrates an 8-arm polyethylene glycol-succinimidyl glutarate (PEG-SG), which constitutes a component of a cross-linked hydrogel, according to one embodiment.
Figure 3:
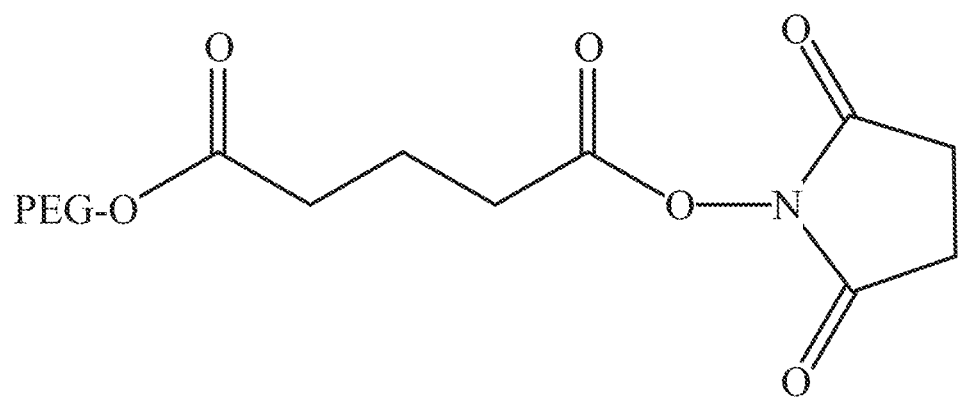
FIG. 3 illustrates an R group for a PEG-SG, which constitutes a component of a cross-linked hydrogel, according to one embodiment.
Figure 4:
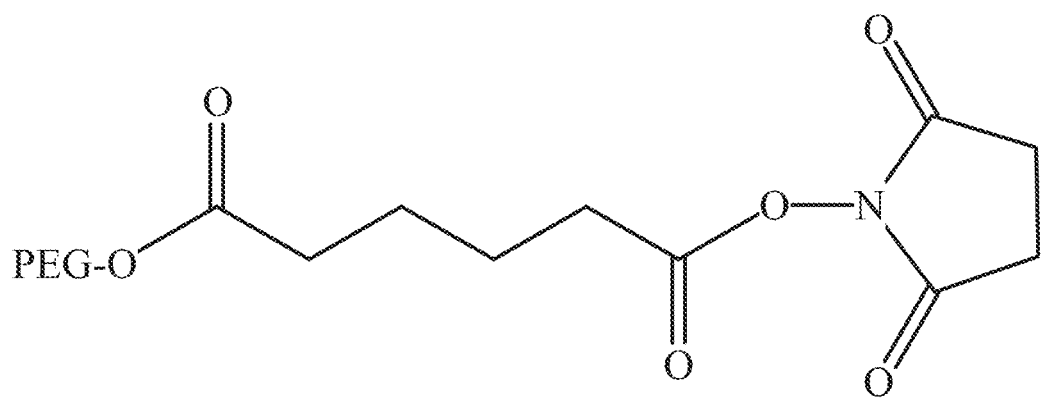
FIG. 4 illustrates an R group for polyethylene glycol-succinimidyl adipate (PEG-SAP), which constitutes a component of a cross-linked hydrogel, according to one embodiment.
Figure 5:
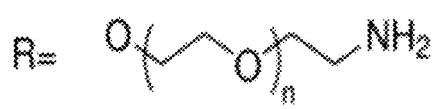
FIG. 5 illustrates an 8-arm polyethylene glycol electrophilic end group (PEG-NH2), which constitutes a component of a cross-linked hydrogel, according to one embodiment.
Figure 5:
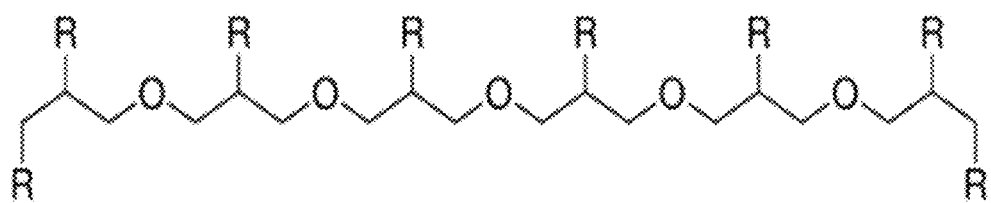

The PEG component of the composite implant comprises a PEG with an electrophilic end group (PEG-NHS) and a PEG with a nucleophilic end group (PEG-NH2). The electrophilic PEG can be selected from the group consisting of different chain lengths and different cores (e.g., hexaglycerol and pentaerythritol). In some embodiments the PEG-NHS group includes electrophilic groups such as SG (N-hydroxysuccinimidyl glutarate), SAP (N-hydroxysuccinimidyl adipate), and SAZ (N-hydroxysuccinimidyl azelate). FIG. 2 illustrates an 8-arm polyethylene glycol-succinimidyl glutarate (PEG-SG), FIG. 3 illustrates an R group for a polyethylene glycol-succinimidyl glutarate (PEG-SG), and FIG. 4 illustrates an R group for polyethylene glycol-succinimidyl adipate (PEG-SAP). A difference in the number of methylene units (spacers) between the functional group and the core can affect degradation and release: SG=3 spacers, SAP=4 spacers, and SAZ=7 spacers. The electrophilic and hydrophilic PEG groups cross-link to form a mesh-like delivery system as depicted in FIG. 1. FIG. 5 illustrates an exemplary embodiment of an 8-arm PEG-NH2.

The hydrogel may be optimized for mesh size (opening between cross-linking), therapeutic agent release rate, and erosion kinetics by varying the cross-linking density (4-arm, 6-arm, and 8-arm PEGs), linker chain length (longer chains=slower hydrolysis and slower release), and PEG molecular weight (the higher molecular weight, the larger the pore size and the faster the release). The PEG core may also be optimized to alter cross-linking and erosion.

The therapeutic complex is composed of a therapeutic agent (i.e., therapeutic protein, etc.) associated with mesoporous silica. The therapeutic agent may be associated with the mesoporous silica by, for example, but not to be limited to, being: 1) dispersed within the mesoporous silica; 2) coated onto the mesoporous silica; 3) adsorbed onto mesoporous silica; or 4) any combination thereof. The association between the therapeutic agent and the mesoporous silica may be achieved and the therapeutic complex may be fabricated by hot melt extrusion, blending, compression, granulation, roller compaction, spray drying, co-lyophilizing, spray freeze drying, microencapsulation, melt encapsulation, coacervation, solvent casting, microfluidics, injection molding, and any other technique for fabricating complexes or microparticles known in the art. Other materials suitable for the complex material may include polyanhydrides and poly(ortho esters).

The hydrogel is manufactured by dissolving the PEG-NHS in dichloromethane (DCM) or water in a vial. The PEG-NH2 is then dissolved in DCM or water in a separate vial and a formulation comprising the therapeutic agent (e.g., a therapeutic protein) is added. The two vials may be mixed with or without triethylamine to catalyze a reaction to form a protein-loaded cross-linked hydrogel. The mixture can be molded or extruded to form the final delivery system or formed in situ. The cross-linking reaction proceeds via the mechanism shown in FIGS. 6A and 6B. Various other mechanisms may be used to achieve a cross-linked polymer hydrogel.

Figure 6A:
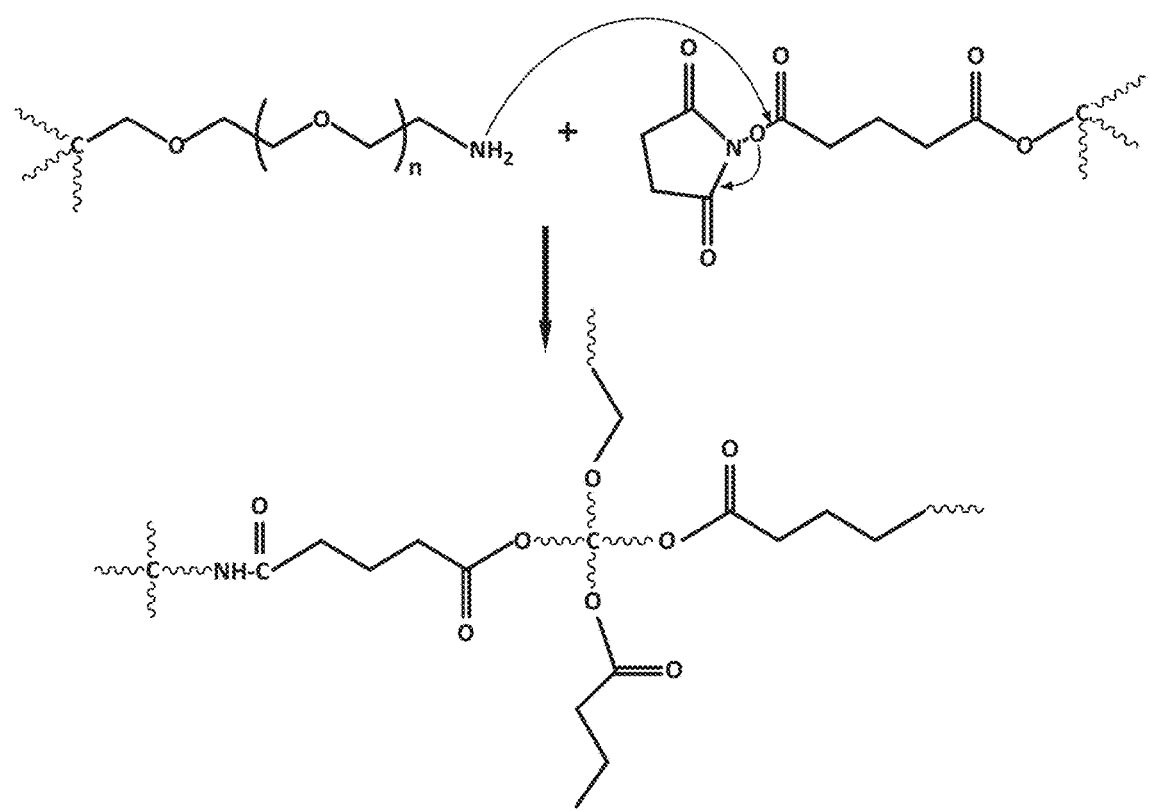
FIG. 6A illustrates a cross-linking reaction via the illustrated mechanism, according to one embodiment.

FIG. 6A illustrates an exemplary cross-linking reaction. The reactants are polyethylene oxide-amine and polyethylene oxide-succinimidyl glutarate which react to produce a product at a pH between 7.4-8. The product may be a crosslinked network with hydrolytically labile ester linkages.

Figure 6B:
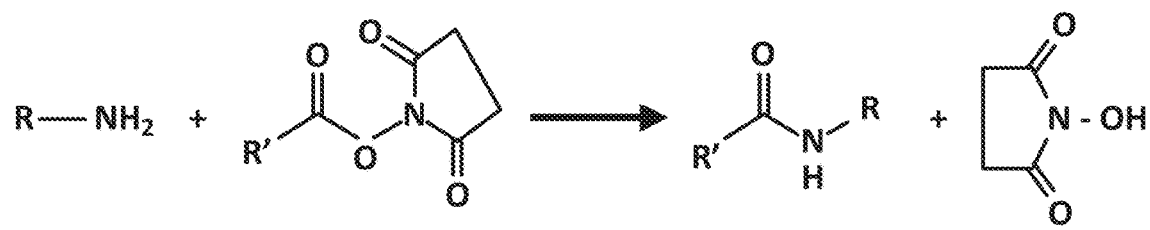
FIG. 6B illustrates a cross-linking reaction via the illustrated mechanism, according to one embodiment.

FIG. 6B illustrates another exemplary cross-linking reaction. The reactants are an amine compound and NHS ester derivative to produce an amide bond compound and an NHS leaving group.

The formulation comprising the therapeutic agent may be prepared by standard techniques or methods that are well-known in the art using one or more pharmaceutically acceptable carriers or excipients. The term "pharmaceutically acceptable," as used herein, means a substance that does not substantially interfere with the effectiveness or the biological activity of the active ingredient (or ingredients) and which is not toxic to the patient in the amounts used. Examples of pharmaceutically acceptable carriers include sterile liquids, such as water and oils, including those of petroleum, animal, vegetable or synthetic origin, such as peanut oil, soybean oil, mineral oil, and sesame oil. Aqueous carriers, including water, are typical carriers for pharmaceutical compositions prepared for intravenous administration. As further examples, saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, and ethanol. The composition, if desired, can also contain wetting or emulsifying agents, or pH buffering agents. Pharmaceutical formulation practices, carriers, and excipients are described in, e.g., Remington Essentials of Pharmaceutics (L. A. Felton ed., 2012). Additional excipients may include polymers such as poly lactic acid, poly (lactic-co-glycolic) acid, cellulosic polymers such as methylcellulose, hydroxypropyl methylcellulose, carboxymethylcellulose, ethyl cellulose, block co-polymers such as poloxamers and polyacrylic acids such as carbomers.

The mesoporous silica particles minimize aggregation of the therapeutic agent and maintain the stability of the therapeutic complex by limiting exposure of the therapeutic agent to the aqueous media of the eye and restricting its molecular mobility within the hydrogel. The hydrogel matrix degrades over the course of weeks to months to sustain the release of the therapeutic agent.

In some embodiments, the mesoporous silica particles may comprise a pore size ranging from 6 to 15 nm. In some embodiments, the mesoporous silica particles may comprise a particle size ranging from 1 to 25 microns. In some embodiments, the mesoporous silica particles may undergo surface modifications to alter the surface charge to the mesoporous silica particles.

The therapeutic complex comprising the therapeutic agent and the mesoporous silica dispersed in the hydrogel matrix may increase the sustained release of the therapeutic agent. In the absence of the bioerodible hydrogel matrix, the therapeutic complex may release the therapeutic agent over a period that is less than 28 days.

In some embodiments, the composite implant releases the therapeutic agent over a period of one week to 12 months from implantation in an eye of a subject, while maintaining the therapeutic agent activity. In some embodiments, the composite implant releases the therapeutic agent for a period of at least six months from implantation in an eye of a subject.

In some embodiments, the composite implant may exhibit a burst release of the therapeutic agent that is less than about 10% (w/w) over an initial 24-hour period from implantation in an eye of a subject. In some embodiments, the composite implant may exhibit a burst release of the therapeutic agent that is less than about 5% (w/w) over an initial 24-hour period from implantation in an eye of a subject.

The release rate of the therapeutic agent from the composite implant may be substantially constant. For example, in some embodiments, the release rate of the therapeutic agent from the composite implant may be substantially constant over an initial three-month period starting at the end of the burst release or lag phase of the therapeutic agent, but not more than 14 days after implantation or in vitro release studies. The lag phase may be defined as the period immediately post-implantation or immediately after initiating in vitro release studies where no drug is released or the drug is released at a slower rate than the constant rate achieved after not more than 14 days.

The release rate of the therapeutic agent from the composite implant may be near-zero order or pseudo-zero order. For example, in some embodiments, the release rate of the therapeutic agent from the composite implant may be near-zero order or pseudo-zero order over an initial three-month period from implantation starting at the end of the burst release or lag phase of the therapeutic agent. Near-zero order release and pseudo-zero order release kinetics may be defined as an essentially linear relationship between the cumulative amount of therapeutic agent released from the composite hydrogel in vivo or in vitro release studies as a function of time.

The composite implant may be introduced, implanted, injected or otherwise delivered into an eye of a subject or a patient. The composite implant may be delivered by implanting the composite implant through a pars-plana injection into a vitreous or posterior chamber of an eye of the subject with a single use application through a needle. In some embodiments, the needle may be less than about 19 gauge, less than about 20 gauge, less than about 21 gauge, less than about 22 gauge, less than about 25 gauge, or other appropriate diameter. In particular embodiments, the needle is a 21 gauge or smaller diameter needle.

The present disclosure also provides methods related to the use of composite implants. In certain embodiments, the present disclosure provides methods of introducing a therapeutic agent into an eye of a subject. Such methods comprise delivering a composite implant as described above into an eye of a subject. In other embodiments, the present disclosure provides methods of treating an ocular disease in a subject that comprise delivering a composite implant as described above to an eye of the subject. The ocular disease may be selected from at least one of neovascular AMD, diabetic macular edema, and macular edema following retinal vein occlusion.

The present disclosure also provides a therapeutic agent for use in treating an ocular disease, wherein the therapeutic agent is provided in a composite implant as described above. Furthermore, the present disclosure provides for use of a therapeutic agent in the manufacture of a composite implant as described above for treatment of a subject in need thereof. The present disclosure also provides a pre-loaded injector assembly comprising a needle and a composite implant as described above.

EXAMPLES

To further illustrate these embodiments, the following examples are provided. These examples are not intended to limit the scope of the claimed invention, which should be determined solely on the basis of the attached claims.

Example 1—an Aflibercept PEG Hydrogel Implants without the Composite Core

Figure 7:
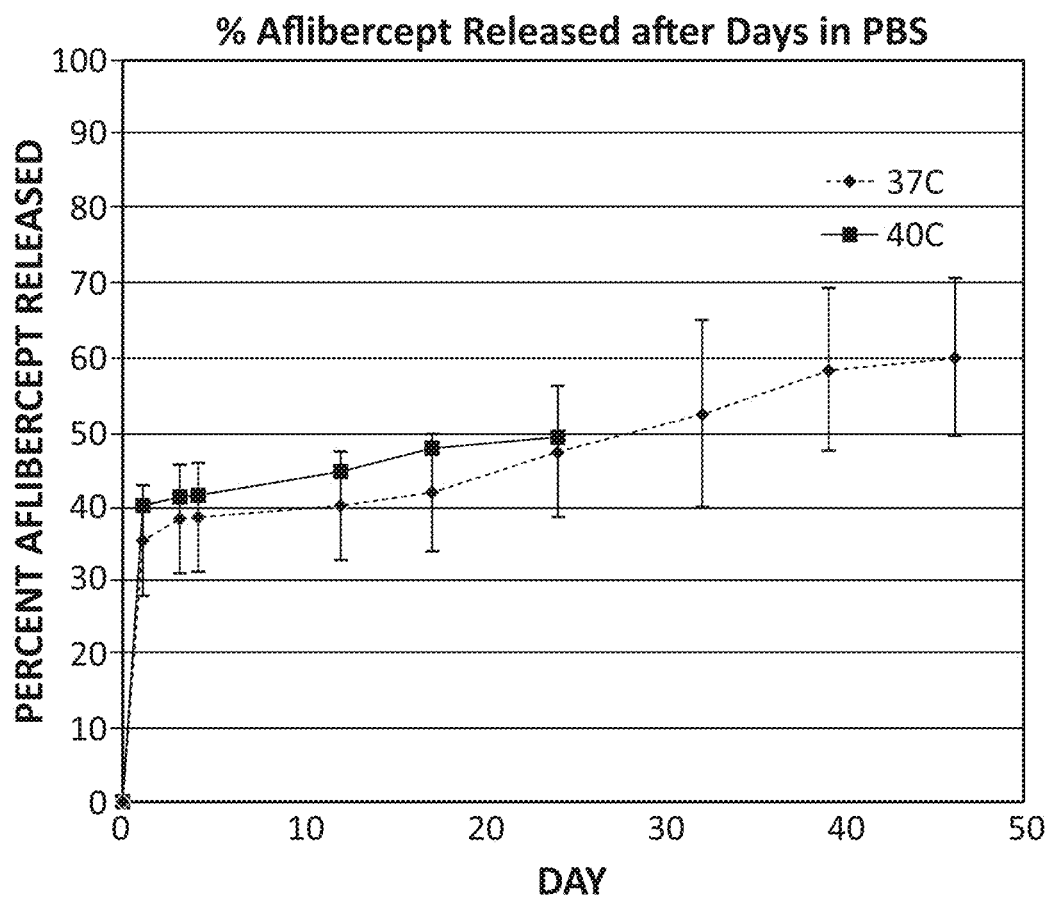
FIG. 7 is a graph showing in vitro release of aflibercept from PEG-SG into isotonic phosphate buffered saline, pH 7.4 at 37° C. and 40° C., according to one embodiment.

This example describes biodegradable hydrogels of cross-linked PEG with a lyophilized aflibercept core were made by dissolving the PEG reagents in DCM according to the formulation in Table 1. The aflibercept core was manufactured by co-lyophilizing aflibercept with (150 mg/mL) in solution of sodium acetate buffer (pH 5.2, 150 mM), histidine (20 mM), arginine (150 mM), methionine (5 mg/mL), P407 (100 mg/mL) and PS 20 (0.05%). The in vitro release of aflibercept was assessed. Loaded hydrogels were placed into 5 mL glass vials containing isotonic phosphate buffered saline (IPBS) at pH 7.4 as the release media. The vials were then placed on a shaker bath to agitate the medium at 37° C. At pre-determined timepoints the media was sampled and the entire receiver media was replaced with fresh IPBS. The aflibercept concentration in the sampled aliquot was quantified by HPLC using a Waters Alliance e2695 system with a C-18 BEH column. The aflibercept concentrations were used to define the cumulative in vitro release of aflibercept from the implant as well as the daily aflibercept release rate. The cumulative in vitro release of aflibercept as a function of time is depicted in FIG. 7. A first graph line occurs at 37° C. and the second graph line occurs at 40° C. As can be seen in Table 2 significant aggregation of aflibercept begins on day 39.

TABLE 1

Aflibercept hydrogel formulation

| Name | PEG-Amine Reagent | PEG-NHS Reagent | % Aflibercept Formulation Loading | % Pure Aflibercept Loading |
|---|---|---|---|---|
| 5AFSP | 4-arm PEG-NH2 10 KDa | 8-arm PEG-SAP 5 KDa | 30.2% | 15% |

TABLE 2

Aggregates and degradants of aflibercept in the release media as a function of time

| Day | % Dimer | % Aggregates |
|---|---|---|
| 0 | 100 | 0 |
| 1 | 100 | 0 |
| 3 | 100 | 0 |
| 4 | 100 | 0 |
| 12 | 100 | 0 |
| 17 | 100 | 0 |
| 24 | 100 | 0 |
| 32 | 97 | 3 |
| 39 | 88 | 12 |
| 46 | 35 | 65 |

Manufacture of aflibercept hydrogels without loss of protein activity and release over 30 to 60 days was achieved. However, aflibercept started aggregating and degrading after 30 days in the cross-linked non-composite PEG hydrogels.

Figure 8:
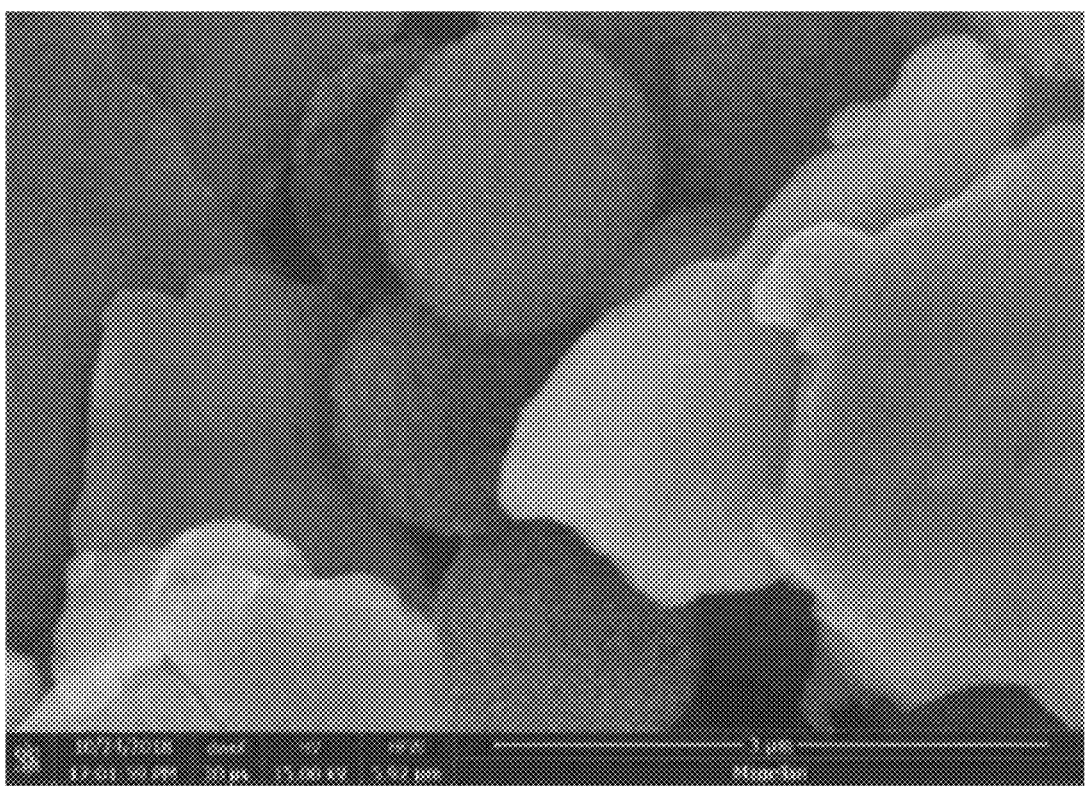
FIG. 8 illustrates a magnified view of mesoporous silica particles lyophilized with P407, according to one embodiment.

Example 2—Aflibercept PEG Hydrogel Implants with a Mesoporous Silica Composite Core The spherical mesoporous silica particles in our first study were manufactured by Glantreo, with a particle size 1.7 µm, pore size of 20 nm and pore volume of 0.74 cm3/g. They were synthesized with the use of TEOS as the precursor under basic catalysis and CTAB as the surfactant to direct morphology of the circular pores. FIG. 8 depicts the particles lyophilized with P407.

The loading of aflibercept within the mesoporous silica particles was performed as follows. The aflibercept was buffer-exchanged from its source and dissolved in a phosphate buffer (pH 5.8) at a concentration of 1 mg/mL. The mesoporous silica particles were dissolved at the same concentration in the buffered solution mixed with a magnetic stir bar for 24 hours. After 24 hours, the solution was transferred to 5 mL polypropylene centrifuge tubes and centrifuged to separate particles from solution containing free aflibercept. The particles were re-suspended, rinsed and centrifuged again to separate loosely adsorbed aflibercept. The solutions containing free aflibercept were sampled. The aflibercept concentration in the sampled aliquot was quantified by HPLC using a Waters Alliance e2695 system with a C-18 BEH column. The aflibercept loading on the mesoporous silica particles was determined via mass balance. The composition of the aflibercept loaded mesoporous silica particles is shown in Table 3.

TABLE 3

Aflibercept-loaded silica formulation

| Sample | Aflibercept Formula | Drying Method | Pure Aflibercept Loading |
|---|---|---|---|
| 4SiAF | Adsorbed to Mesoporous Silica, 20 nm pores, 1.7 um | Vacuum Dried | 37% |

Release of the aflibercept from the mesoporous silica particles was assessed in vitro. Particles were weighed into 5 mL glass vials containing isotonic phosphate buffered saline (IPBS) at pH 7.4 as the release media. The vials were then placed on a shaker bath to agitate the medium at 37° C. At pre-determined time points the media was sampled and the entire receiver media was replaced with fresh IPBS. The aflibercept concentration in the sampled aliquot was quantified by HPLC using a Waters Alliance e2695 system with a C-18 BEH column. The aflibercept concentrations were used to define the cumulative in vitro release of aflibercept from the implant as well as the daily aflibercept release rate.

Figure 9:
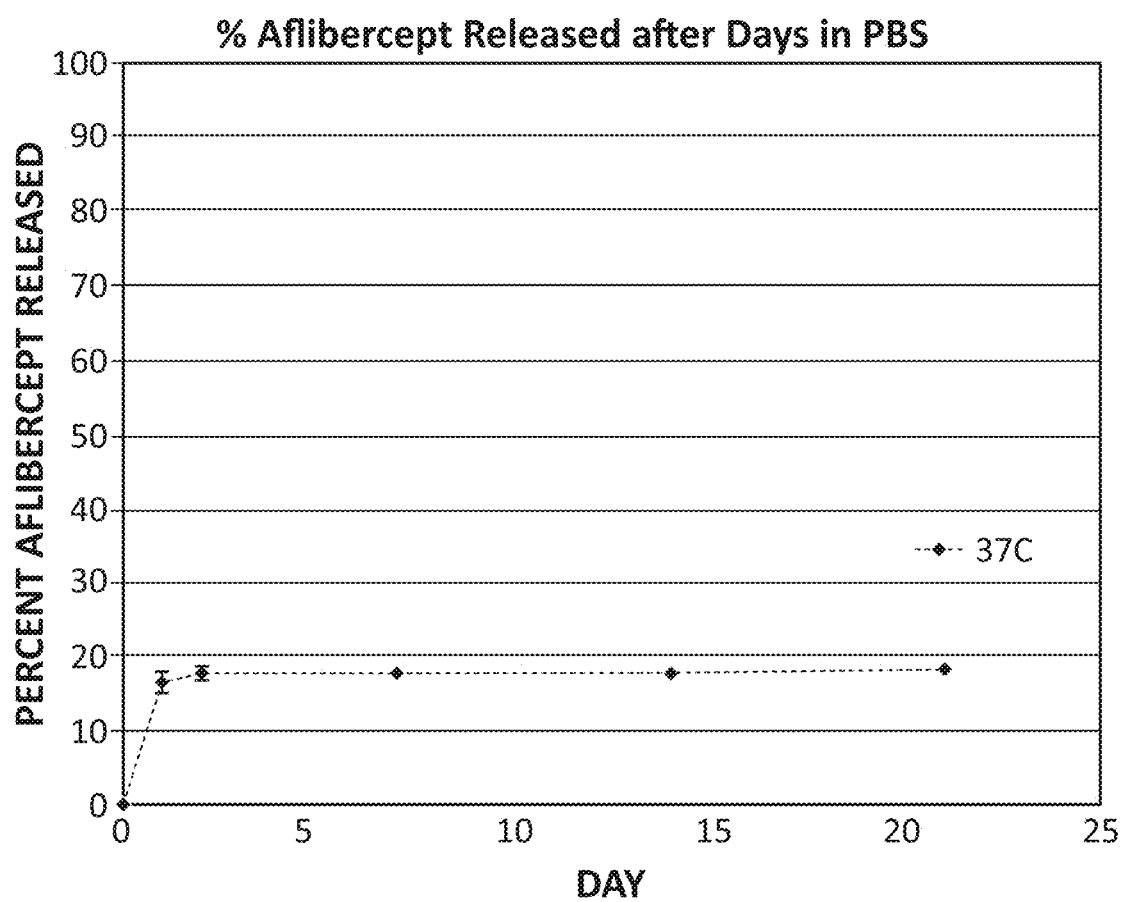
FIG. 9 is a graph of in vitro release of aflibercept from loaded mesoporous silica particles at 37° C., according to one embodiment.
Figure 10:
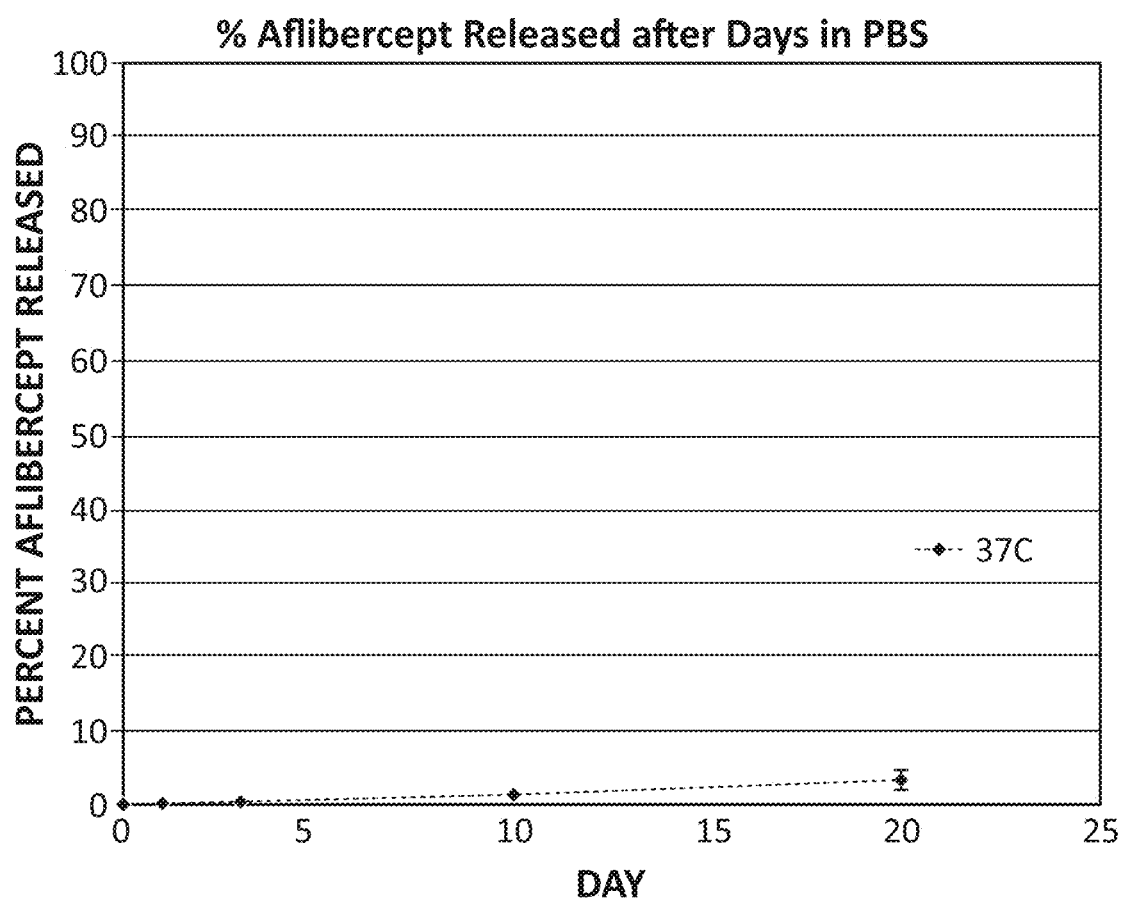
FIG. 10 is a graph of in vitro release of aflibercept from loaded mesoporous silica particles at 37° C., according to one embodiment.

With no hydrogel to sequester the particles, mesoporous silica particles that were lyophilized or vacuum-dried exhibited a 20% burst release, followed by little to no release afterwards, as shown in FIG. 9. In a hydrogel only implant, a substantial portion of protein was released from the formulation following aqueous exposure, as shown in FIG. 7. Surprisingly, entrapping the protein-loaded mesoporous silica particles within the PEG hydrogel mitigates the burst release observed as shown in FIG. 10. The hydrogel mitigates the rate of release, which is dependent on molecular weights (5KD, 10KD) of the PEG monomers, crosslinking density, the NHS ester group (SG, SAP, SAZ) and the number of arms (4-arm, 8-arm). The mesoporous silica particles also affect the release of the protein, which is also dependent on the size and shape of particles, pore structure, pore size and surface area of exposed pores.

The mesoporous silica/hydrogel composite implant was manufactured by dissolving the PEG-NHS in phosphate buffer (pH 7.4) or water in a vial. The PEG-NH2 is then dissolved phosphate buffer or water in a separate vial and the protein-loaded mesoporous silica particles are added to the same vial. The two vials are mixed and the cross-linking reaction is initiated. The mixture can be molded or extruded to form the final delivery system. The composition is shown in Table 4.

TABLE 4

Aflibercept/mesoporous silica composite hydrogel formulation

| Sample | Aflibercept Formula | PEG Ester | PEG Amine | Pure Aflibercept Loading |
|---|---|---|---|---|
| 4SiAFHGL | Adsorbed to Mesoporous Silica, 20 nm pores, 1.7 um | 8-arm PEG SG-10K | 8-arm PEG NH2-10K | 18% |

The mesoporous silica particles reduced aflibercept burst significantly and demonstrated slow sustained release. The pore size of the mesoporous silica particles can be optimized to achieve the desired release rate. A further advantage of the mesoporous silica particle compositions is that it may enable aqueous manufacturing, thereby avoiding harsh and potentially unsafe organic solvents. Unique attributes to this composite system include: stabilization of protein during in vitro and in vivo release; a pseudo zero order release rate of protein from the composite hydrogel; a protein burst release less than 10% over the first day; and the ability to release stabile protein while maintaining stability and activity over a period of six months.

Figure 11:
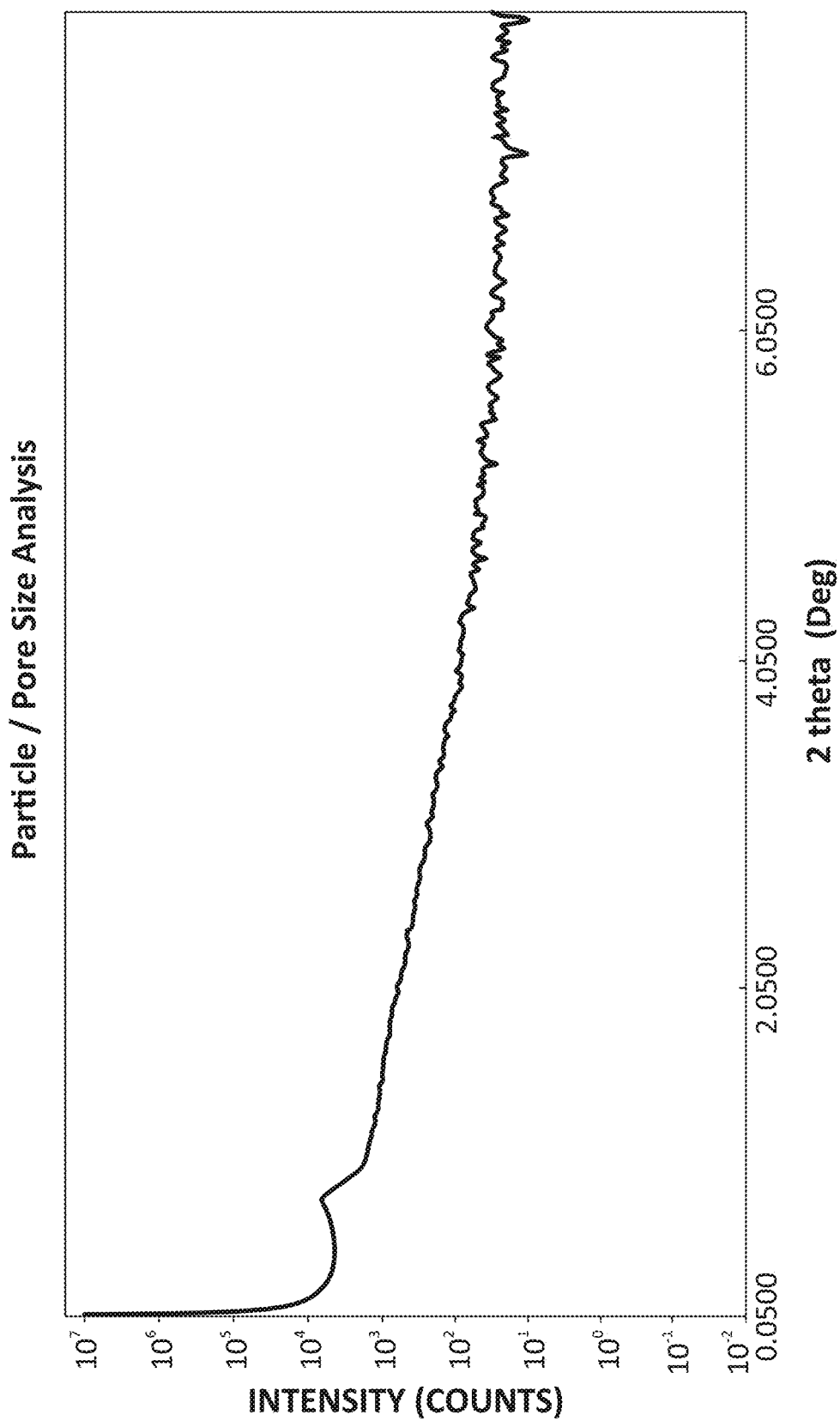
FIG. 11 is a small angle x-ray diffraction (SAX) defractogram of mesoporous silica particles, according to one embodiment.

The Glantreo mesoporous silica particles used in this experiment were determined to have very poor pore structure by SAX as shown in FIG. 11. The lack of sharp reflections at (100), (110) and (200) indicate poor to no order. The actual pore size could not be determined due to the high polydispersity of the pores.

Example 3—Aflibercept PEG Hydrogel Implants with a Mesoporous Silica Composite Core A second series of mesoporous silica particles were produced utilizing the pluronic P123 as the surfactant template. This surfactant may make larger pore sizes than CTAB. The method follows the procedure described in Katiyar et al./J. Chromatogr. A 1122 (2006) 13-20. The method may comprise (1) 3 grams of P123 was dissolved in 60 ml (1.5M) HCl; (2) 0.6 grams of CTAB and TMB (ratio shown in Table 5) was mixed with 25 mL de-ionized water separately; (3) Both solutions were mixed together thoroughly as 20 mL of ethanol (100%) was added; (4) 10 mL of TEOS was added drop by drop to the surfactant solution and the mixture was stirred at 600 rpm for 45 minutes at 35° C.; (5) the mixture was then transferred to stoppered PTFE bottle and stored under static conditions at 75° C. for 10 hours followed by hydrothermal swelling at 115 to 125° C. for 8 hours; (6) the mesoporous silica thus formed was filtered, rinsed with de-ionized water and then dried under vacuum; and (7) the dried mesoporous silica particles were calcined at 500° C. with a heating rate of 1° C./min and cooling of 5° C./min.

Figure 12:
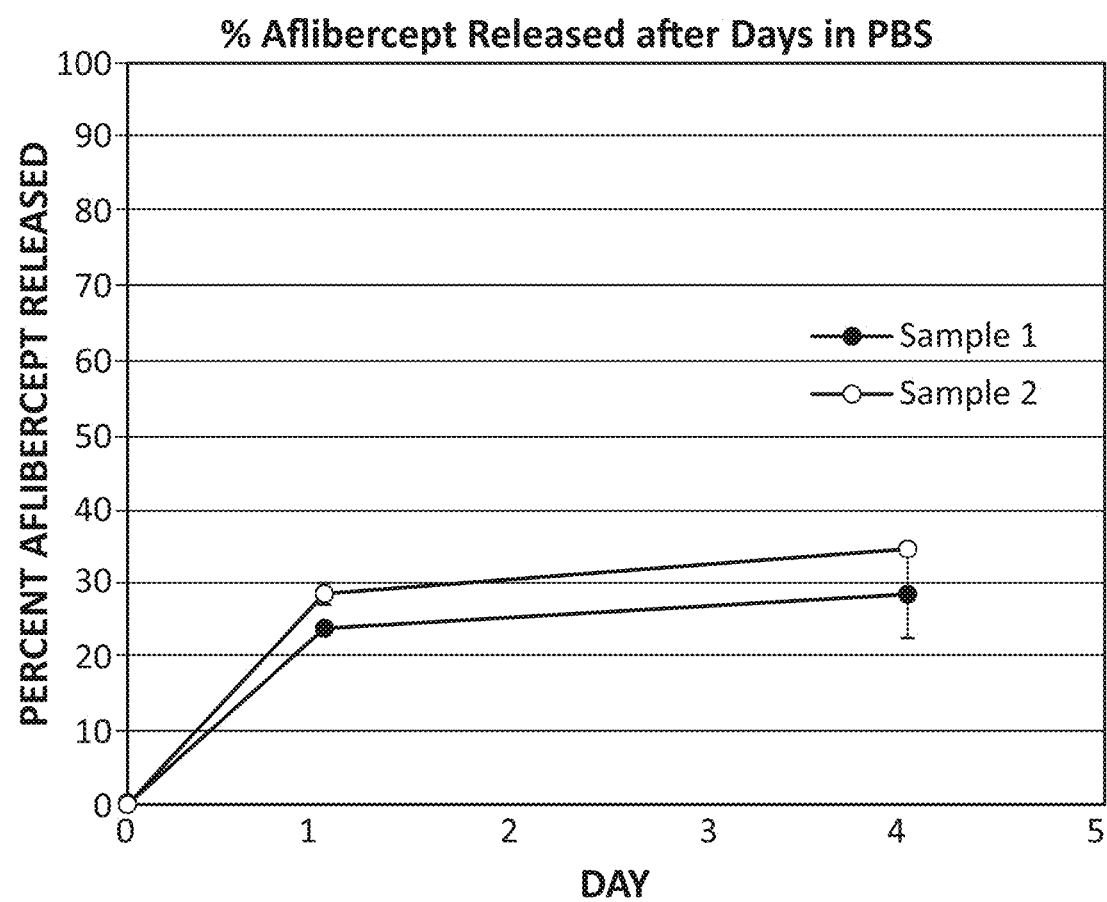
FIG. 12 is a graph of in vitro release of aflibercept from a variety of loaded mesoporous silica composite hydrogel formulations, according to one embodiment.

Aflibercept was loaded onto the calcined mesoporous silica particles and entrapped in the hydrogel matrix as described above. The in vitro release of aflibercept from the hydrogel matrix was conducted as described above. The release profile for the first four days is depicted in FIG. 12. It can be seen that slow sustained release of aflibercept from the mesoporous silica particles/hydrogel is achieved for the first four days.

TABLE 5

Aflibercept/mesoporous silica composition 2

| Lot Name | Silica Batch | Silica Mass (mg) | TMB:P123 Ratio | Aging Temp | Aging Time | % Aflibercept Loading in Silica |
|---|---|---|---|---|---|---|
| Sample 1 | MSFP2 | 8.69 | 0.25 | 115 C. | 24 hrs | 3.77 |
| Sample 2 | MSFP3 | 14.95 | 0.35 | 125 C. | 72 hrs | 10.15 |

Entrapping the protein within mesoporous silica particles and sequestering them in a cross-linked hydrogel matrix extends the duration of release, mitigates burst and stabilizes the protein for an extended period of time. With the hydrogel alone, protein stability is lost after 30 days. Combining the two systems allows for a highly tunable release profile dependent on the PEG characteristics as well as the morphology of the mesoporous particles and their pores. Specifically, the hydrogel determines the primary rate of release, which is dependent on molecular weights (5KD, 10KD) of the PEG monomers, cross-linking density, the NHS ester group (SG, SAP, SAZ) and the number of arms (4-arm, 8-arm). The mesoporous silica particles secondarily affect the release of the protein, which is also dependent on the size and shape of particles, pore structure, pore size and surface area of exposed pores.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A composite implant comprising:
   a bioerodible cross-linked polyethylene glycol hydrogel; and
   a therapeutic complex comprising:
      a therapeutic agent selected from a protein or a peptide; and
      mesoporous silica particles;
      wherein the therapeutic complex is dispersed in the bioerodible cross-linked polyethylene glycol hydrogel,
   wherein the composite implant is capable of being implanted in a vitreous chamber of an eye of a subject and stabilizing the therapeutic agent against aggregation and degradation for at least six months after implantation,
   wherein the bioerodible cross-linked polyethylene glycol hydrogel comprises a network of polyethylene glycol formed by a reaction between a polyethylene glycol with an electrophilic end group and polyethylene glycol with a nucleophilic end group, and
   wherein the electrophilic end group comprises a hydroxysuccinimidyl glutarate (SG), an N-hydroxysuccinimidyl adipate (SAP), or an N-hydroxysuccinimidyl azelate (SAZ).

2. The composite implant of claim 1, wherein a burst release of the therapeutic agent from the composite implant ranges from between about 0 and about 5 percent (w/w) over an initial 24-hour period from implantation in an eye of a subject.

3. The composite implant of claim 1, wherein the release rate of the therapeutic agent from the composite implant is substantially constant over an initial three-month period beginning with the end of the burst release or lag phase, but not more than 14 days post-implantation.

4. The composite implant of claim 3, wherein the release rate of the therapeutic agent from the composite implant is near-zero order or pseudo-zero order over an initial three-month period from implantation beginning with the end of the burst release or lag phase, but not more than 14 days post-implantation.

5. The composite implant of claim 1, wherein the composite implant releases the therapeutic agent for a period of at least six months from implantation in an eye of a subject.

6. The composite implant of claim 1, wherein the therapeutic complex releases the therapeutic agent over a period that is less than 28 days in the absence of the bioerodible cross-linked polyethylene glycol hydrogel.

7. The composite implant of claim 1, wherein the mesoporous silica particles comprise a pore size ranging from 6 to 15 nm.

8. The composite implant of claim 1, wherein the mesoporous silica particles comprise particles ranging from 1 to 25 microns.

9. The composite implant of claim 1, wherein a surface of the mesoporous silica particles comprises a charge.

10. The composite implant of claim 1, wherein the therapeutic agent is selected from at least one of bevacizumab, ranibizumab, aflibercept, brolucizumab, faricimab, conbercept, ankyrin repeat proteins, adalimumab, anti-TNF-alpha agents, biosimilars, or salts, esters, solvates, isomers, complexes, or conjugates thereof.

11. The composite implant of claim 1, wherein the therapeutic agent is adsorbed to the mesoporous silica particles.

12. A pre-loaded injector assembly comprising:
   a needle; and
   a composite implant comprising:
      a bioerodible cross-linked polyethylene glycol hydrogel; and
      a therapeutic complex comprising:
         a therapeutic agent selected from a protein or a peptide; and
         mesoporous silica particles,
      wherein the complex is dispersed in the bioerodible cross-linked polyethylene glycol hydrogel, and
   wherein the composite implant is loaded in the needle,
   wherein the composite implant is capable of being implanted in a vitreous chamber of an eye of a subject and stabilizing the therapeutic agent against aggregation and degradation for at least six months after implantation,
   wherein the bioerodible cross-linked polyethylene glycol hydrogel comprises a network of polyethylene glycol formed by a reaction between a polyethylene glycol with an electrophilic end group and polyethylene glycol with a nucleophilic end group, and
   wherein the electrophilic end group comprises a hydroxysuccinimidyl glutarate (SG), an N-hydroxysuccinimidyl adipate (SAP), or an N-hydroxysuccinimidyl azelate (SAZ).

13. The pre-loaded injector assembly of claim 12, wherein the composite implant provides a burst release of the therapeutic agent ranging from between about 0 and about 5 percent (w/w) over an initial 24-hour period after delivery to the vitreous chamber.

14. A method of introducing a therapeutic agent into an eye of a subject, the method comprising:
   delivering a composite implant to a vitreous chamber of an eye of a subject, the composite implant comprising:
      a bioerodible cross-linked polyethylene glycol hydrogel; and
      a therapeutic complex comprising:
         a therapeutic agent selected from a protein or a peptide; and
         mesoporous silica particles;
         wherein the therapeutic complex is dispersed in the bioerodible cross-linked polyethylene glycol hydrogel,
   wherein the composite implant is capable of stabilizing the therapeutic agent against aggregation and degradation for at least six months after delivery to the vitreous chamber,
   wherein the bioerodible cross-linked polyethylene glycol hydrogel comprises a network of polyethylene glycol formed by a reaction between a polyethylene glycol with an electrophilic end group and polyethylene glycol with a nucleophilic end group, and
   wherein the electrophilic end group comprises a hydroxysuccinimidyl glutarate (SG), an N-hydroxysuccinimidyl adipate (SAP), or an N-hydroxysuccinimidyl azelate (SAZ).

15. The method of claim 14, wherein the delivering a composite implant to the vitreous chamber of an eye of a subject comprises injecting the composite implant through a pars-plana injection into the vitreous chamber.

16. The method of claim 14, wherein the composite implant provides a burst release of the therapeutic agent ranging from between about 0 and about 5 percent (w/w) over an initial 24-hour period after delivery to the vitreous chamber.

* * * * *